United States Patent [19]

Yasohara et al.

[11] Patent Number: 5,565,345

[45] Date of Patent: Oct. 15, 1996

[54] PROCESS FOR PREPARING THIENOTHIOPYRAN DERIVATIVE

[75] Inventors: Yoshihiko Yasohara, Himeji; Yoshiko Tari, Takasago; Noboru Ueyama, Kobe; Junzo Hasegawa, Akashi; Satomi Takahashi, Kobe, all of Japan

[73] Assignee: Kanegafuchi Kagaku Kogyo Kabushiki Kaisha, Osaki, Japan

[21] Appl. No.: 380,334

[22] Filed: Jan. 30, 1995

Related U.S. Application Data

[63] Continuation of Ser. No. 125,672, Sep. 24, 1993, abandoned.

[30] Foreign Application Priority Data

Sep. 28, 1992 [JP] Japan ................................. 4-257822

[51] Int. Cl.⁶ ............................. C12P 11/00; C12P 17/18; C12P 17/00; C07D 409/04
[52] U.S. Cl. ......................... 435/117; 435/119; 435/130; 435/280; 549/23
[58] Field of Search ............................. 549/23; 435/117, 435/119, 130, 280

[56] References Cited

U.S. PATENT DOCUMENTS

| | | | |
|---|---|---|---|
| 4,857,468 | 8/1989 | Kutsuki et al. | 435/280 |
| 5,102,793 | 4/1992 | Petzoldt et al. | 423/280 |
| 5,157,129 | 10/1992 | Blacklock et al. | 549/23 |
| 5,266,485 | 11/1993 | Sawa et al. | 435/280 |

FOREIGN PATENT DOCUMENTS

WO9405802  3/1994  WIPO.

OTHER PUBLICATIONS

Chemical Abstracts, vol. 113, 1190, Abs. #170436r, Bille–Abdullah et al, "Studies on microbial reduction of cyclopentanoic ketones," Dechema Biotechnol. Conf. 1989, 3, p. 249.

CA:105 1986, Abs. #132095f, Mironowicz et al, "Biotransformations. XIX. Reduction of some terpeniz ketones by means of immobilized cells of Rhodotorula . . . " Acta Biotechnol, 1986, vol. 4 p. 141.

CA:105, 1986, Abs. #207607k, Okami et al, "Optically active 1–(4–phenoxyphenoxy) propan–2–01 by microbial reduction of corresponding ketone," JP61,108,394 27 May 1986.

Imuta et al, "Product Stereospecificity in the Microbial Reduction of β–Haldaryl Ketones," J. Org. Chem., 1980, vol. 45, pp. 3352–3355.

"An symmetric Synthesis of MK–0417. Observations on Oxazaborolidine—Catalyzed Reductions," by Todd K. Jones et al. in J. Org. Chem. vol. 56, pp. 763–765 (1991).

Organic Synthesis Collective volumes, 7, pp. 215–220 (1990) corresponds to Org. Synth. 63, 1–9 (1984).

*Primary Examiner*—José G. Dees
*Assistant Examiner*—Mary C. Cebulak

[57] ABSTRACT

A process for preparing 5,6-dihydro-4-hydroxy-(S)-6-methyl-thieno[2,3-b]thiopyran-7,7-dioxide having the formula (II):

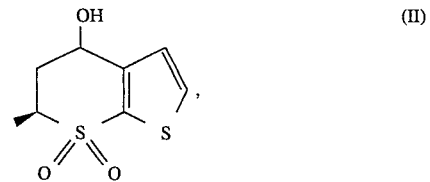

which comprises subjecting 5,6-dihydro-4-oxo-(S)-6-methyl-thieno[2,3-b]thiopyran-7,7-dioxide having the formula (I):

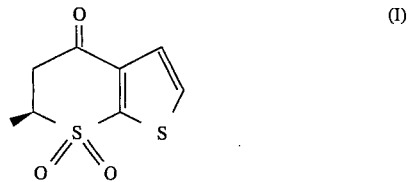

to the action of a microorganism to reduce the thienothiopyran derivative having the formula (I), and collecting 5,6-dihydro-4-hydroxy-(S)-6-methyl-thieno-[2,3-b]thiopyran-7,7-dioxide having the formula (II) from the reaction mixture, wherein said microorganism belongs to the genus selected from the group consisting of Ambrosiozyma, Arthroascus, Ashbya, Candida, Cryptococcus, Hansenula, Kluyveromyces, Lipomyces, Lodderomyces, Metschnikowia, Pachysolen, Pichia, Rhodosporidium, Rhodotorula, Saccharomyces, Saccharomycopsis, Schwanniomyces, Sporidiobolus, Spolobolomyces, Stephanoascus, Trigonopsis, Trichosporon and Wingea, according to which, a simple and effective. process for preparing 5,6-dihydro-4-hydroxy-(S)-6-methyl-thieno-[2,3-b]thiopyran-7,7-dioxide.

1 Claim, No Drawings

PROCESS FOR PREPARING THIENOTHIOPYRAN DERIVATIVE

This application is a continuation of Ser. No. 08/125,672, filed Sep. 24, 1993, now abandoned.

BACKGROUND OF THE INVENTION

The present invention relates to a process for preparing 5,6-dihydro-4-hydroxy-(S)-6-methyl-thieno-[2,3-b]thiopyran-7,7-dioxide having the formula (II):

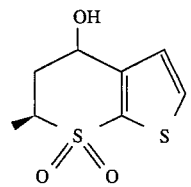

The above-mentioned thienothiopyran derivative (II) of the invention is a useful synthetic intermediate which can be converted by an organic chemical method which is conventionally used, into the drug for glaucoma MK-507 having the formula (III):

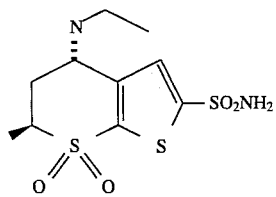

(Fortoshuritte der Ophthalmologie 88, p513, 1991).

Therefore, it has been desired to develop a process for preparing the above-mentioned thienothiopyran derivative having the formula (II) which enables efficient production on an industrial scale.

However, any satisfiable process has not been known until now. No document describes a process for preparing 5,6-dihydro-4-hydroxy-(S)-6-methyl-thieno-[2,3-b]thiopyran-7,7-dioxide having the formula (II), which comprises reducing 5,6-dihydro-4-oxo-(S)-6-methyl-thieno-[2,3-b]thiopyran-7,7-dioxide having the formula (I):

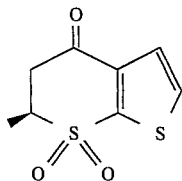

with a microorganism.

The synthesis method described in Japanese Unexamined Patent Publication No. 100174/1989 has been known as the process for preparing the above-mentioned thienothiopyran derivative (III). However, a process comprising the step wherein the thienothiopyran derivative (I) is reduced with a microorganism to give the thienothiopyran derivative (II), is not known.

An object of the invention is to provide a simple and efficient process for preparing the thienothiopyran derivative (II) which can be industrially used.

This and the other objects of the present invention will become apparent from the description hereinafter.

SUMMARY OF THE INVENTION

In accordance with the present invention, there is provided a process for preparing 5,6-dihydro-4-hydroxy-(S)-6-methyl-thieno[2,3-b]thiopyran-7,7-dioxide having the formula (II):

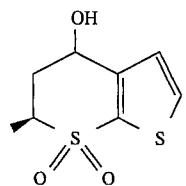

which comprises subjecting 5,6-dihydro-4-oxo-(S)-6-methyl-thieno[2,3-b]thiopyran-7,7-dioxide having the formula (I):

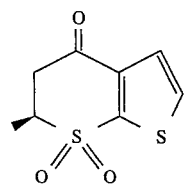

to the action of a microorganism to reduce the thienothiopyran derivative having the formula (I), and collecting 5,6-dihydro-4-hydroxy-(S)-6-methyl-thieno-[2,3-b]thiopyran-7,7-dioxide having the formula (II) from the reaction mixture, wherein said microorganism belongs to the genus selected from the group consisting of Ambrosiozyma, Arthroascus, Ashbya, Candida, Cryptococcus, Hansenula, Kluyveromyces, Lipomyces, Lodderomyces, Metschnikowia, Pachysolen, Pichia, Rhodosporidium, Rhodotorula, Saccharomyces, Saccharomycopsis, Schwanniomyces, Sporidiobolus, Spolobolomyces, Stephanoascus, Trigonopsis, Trichosporon and Wingea.

According to the present inventions, it is possible to efficiently produce 5,6-dihydro-4-hydroxy-(S)- 6-methyl-thieno[2,3-b]thiopyran-7,7-dioxide in an industrial scale, by subjecting 5,6-dihydro-4-oxo-(S)-6-methyl-thieno[2,3-b] thiopyran-7,7-dioxide having the formula (I) to the action of the specified microorganism which can reduce oxygen atom of carbonyl group at the 4-position of the thienothiopyran ring to hydroxyl group. Thus obtained 5,6-dihydro-4-hydroxy-(S)-6-methyl-thieno[2,3-b]thiopyran-7,7-dioxide according to the invention can be used as an intermediate of MK-507 being a drug for glaucoma.

DETAILED DESCRIPTION

A substrate used in the process of the invention is 5,6-dihydro-4-oxo-(S)-6-methyl-thieno[2,3-b]thiopyran- 7,7-dioxide having the formula (I). The above-mentioned thienothiopyran derivative (I) can be prepared by converting (S)-3-(2-mercaptothiophene) butyric acid having the formula (IV):

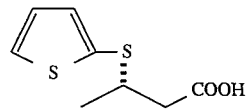

synthesized according to the process described in U.S. Pat. No. 4,968, 814, according to the process described in Japanese Unexamined Patent Publication No. 100174/1989.

Examples of the microorganism used in the process of the present invention are, for instance, the microorganisms belonging to Ambrosiozyma, Arthroascus, Ashbya, Candida, Cryptococcus, Hansenula, Kluyveromyces, Lipomyces, Lodderomyces, Metschnikowia, Pachysolen, Pichia, Rhodosporidium, Rhodotorula, Saccharomyces, Saccharomycopsis, Schwanniomyces, Sporidiobolus, Spolobolomyces, Stephanoascus, Trigonopsis, Trichosporon, Wingea and the like. More particularly, they are, for instance, *Ambrosiozyma philentona* IFO 1847, *Arthroascus javanesis* IFO 1848, *Ashbya gossypii* IFO 0560, *Candida cantarellii* IFO 1261, *Candida guilliermondii* IFO 0454, *Candida intermedia* IFO 0761, *Candida kefyr* IFO 0706, *Candida magnoliae* IFO 0705, *Candida realrosa* ATCC 20275, *Candida maris* IFO 10003, *Candida mogii* IFO 0436, *Candida nusae* IFO 1582, *Candida nodaensis* IFO 19420. *Candida parapsilosis* IFO 0585, *Candida saitoana* IFO 0768, *Candida sorbophila* IFO 1583, *Candida tropicalis* IFO 0589, *Candida tropicalis* IFO 1400, *Candida tropicalis* IFO 1404, *Candida versatilis* IFO 1228, *Cryptococcus albidus* IFO 0378, *Cryptococcus terreus* IFO 0727, *Pichia capsulata* IFO 0721, *Hansenula glucozyma* IFO 1472, *Pichia holstii* IFO 0980, *Pichia minuta* IFO 0975, *Pichia minuta* IFO 1473, *Kluyveromyces marxianus* IFO 0288, *Lipomyces starkeyi* IFO 0678, *Lodderomyces elongisporus* IFO 1676, *Metschnikowia bicuspidata* IFO 1408, *Metschnikowia pulcherrima* IFO 0561, *Metschnikowia reukaufii* IFO 0749, *Pachysolen tannophilus* IFO 1007, *Pichia burtonii* IFO 0844, *Pichia carsonii* IFO 0946, *Pichia toletana* IFO 0950, *Rhodosporidium dacryodium* IFO 1930, *Rhodosporidium sphaerocarpum* IFO 1438, *Rhodosporidium toruloides* IFO 0413, *Rhodotorula glutinis* IFO 0395, *Rhodotorula lactosa* IFO 1423, *Rhodotorula minuta* IFO 0928, *Rhodotorula minuta* IFO 0715, *Saccharomyces cerevisiae* IFO 0258, *Saccharomycopsis crataegensis* IFO 1708, *Saccharomycopsis malanga* IFO 1710, *Schwanniomyces occidentalis* IFO 1840, *Sporidiobolus johnsonii* IFO 6903, *Sporobolomyces pararoseus* IFO 0471, *Stephanoascus ciferrii* IFO 1854, *Trigonopsis variabilis* IFO 0671, *Trichosporon cataneum* IFO 1198. *Wingea robertsii* IFO 1277 and the like.

For culturing the above-mentioned microorganism, a culture medium (a solid culture medium such as an agar medium or a liquid culture medium) containing nutrient components which are used for a culture of a microorganism can be usually employed. In case of mass culture, it is preferable to employ a liquid culture medium. The culture medium may contain for example, sugars such as glucose, sucrose and maltose, organic acids such as lactic acid, acetic acid and citric acid, alcohols such as ethanol and glycerol, or the mixture thereof as a carbon source; and ammonium sulfate, ammonium phosphate, urea, yeast extract, meat extract, peptone or the like as a nitrogen source. Additionally, nutrient sources such as another inorganic salt, vitamins can be optionally mixed therewith. The microorganisms as mentioned above can be cultured under the usual conditions. For example, the microorganism is preferably cultured in the culture medium of pH ranging from 4.0 to 9.5 at a temperature of from 20° to 45° C. for 10 to 96 hours under an aerobic condition.

The substrate, 5,6-dihydro-4-oxo-(S)-6-methyl-thieno-[2,3-b]thiopyran-7,7-dioxide is subjected to the action of the microorganism, usually by mixing the substrate with the culture broth containing, cells of the microorganism as it is. In case that the reaction is influenced for the worse by a constituent contained in the above-mentioned culture broth, a suspension of the cells obtained by centrifuging the culture broth, or by other means may be used instead of the above-mentioned culture broth. The substrate may be added all at once in the earlier stage of the reaction or in portions in the course of the reaction. The reaction is carried out at a temperature ranging usually from 15° to 50 ° C., preferably from 20° to 40° C. at a pH of from 2.5 to 7.0. An amount of cells contained in the reaction mixture may be optionally changed according to a capacity of the cells for contacting with the substrate in the reaction. The substrate concentration is preferably 0.01 to 20% (w/v), more preferably 0.1 to 10% (w/v). The reaction is usually carried out with shaking or with aerobically stirring. The reaction period may be suitably determined according to the substrate concentration, the amount of the used microorganism and other reaction conditions. Usually, it is preferable to determine each reaction condition so that the reaction is completed within 2 to 168 hours. In case that glucose or the like is added to the reaction mixture as an energy source in a proportion of 1 to 5% (w/v) based on the reaction mixture on purpose to accelerate the above-mentioned reaction, good results are obtained in many cases. As the result of the reaction, 5,6-dihydro-4-oxo-(S)-6-methyl-thieno[2,3-b]-thiopyran- 7,7-dioxide being the substrate is reduced to give 5,6-dihydro-4-hydroxy-(S)-6-methyl-thieno[2,3-b]-thiopyran- 7,7-dioxide.

In order to collect thus obtained 5,6-dihydro- 4-hydroxy-(S)-6-methyl-thieno[2,3-b]thiopyran-7,7-dioxide from the reaction mixture, a usual isolation method can be employed. For example, thus obtained thienothiopyran derivative is extracted by adding an organic solvent such as ethyl acetate to the reaction mixture. The resulting extract is dehydrated with anhydrous sodium sulfate or the like, and then the organic solvent is removed under a reduced pressure therefrom. As a result, a crude 5,6-dihydro- 4-hydroxy-(S)-6-methyl-thieno[2,3-b]thiopyran-7,7-dioxide can be obtained. Further, the purified 5,6-dihydro- 4-hydroxy-(S)-6-methyl-thieno[2,3-b]thiopyran-7,7-dioxide can be obtained from the crude product, as occasion demands, by subjecting the crude product to recrystallization.

The final product, 5,6-dihydro-4-hydroxy-(S)- 6-methyl-thieno[2,3-b]thiopyran-7,7-dioxide having the formula (II) may be in the form of the stereoisomer having the formula (IIa) and/or the stereoisomer having the formula (IIb):

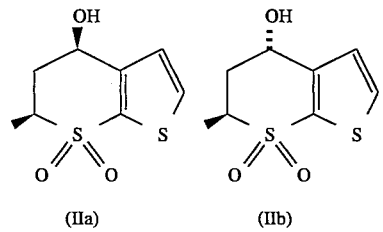

owing to configuration of hydroxy group at the 4-position of the thienothiopyran ring.

The stereoisomer (IIa) is a 4R-isomer and a cis-isomer based on (S)-methyl group at the 6-position of the thienothiopyran ring. The stereoisomer (IIb) is a 4S-isomer and a trans-isomer based on (S)-methyl group at the 6-position thereof.

Among them, the stereoisomer (IIb) can be utilized as an intermediate of MK-507 because the configuration of the substituent at the 4-position of the thienothiopyran ring in the stereoisomer (II b) is the same as that in MK-507.

The proportion of the stereoisomer (II a) and the stereoisomer (IIb) in the resulting thienothiopyran derivative (II) varies in dependence on the strain of the used microorganism. In order to obtain the thienothiopyran derivative (II) containing the stereoisomer (IIb) in a higher proportion, the microorganism may be used which belongs to Candida, Cryptococcus, Pichia, Lipomyces, Metschnikowia, Rhodosporidium, Rhodotorula, Stephanoascus, Trigonopsis, Hansenula, Kluyveromyces, Saccharomyces, Schwanniomyces or Trichosporon. Examples of the above-mentioned microorganism are, for instance, *Candida sorbophila* IFO 0768, *Candida tropicalis* IFO 0589, *Cryptococcus terreus* IFO 0727, *Pichia minuta* IFO 0975, *Lipomyces starkeri* IFO 0678, *Metschnikowia bicuspidsis* IFO 1408, *Metschnikowia reukaufii* IFO 0749, *Pichia roletans* IFO 0950, *Rhodosporidium toruloides* IFO 0413, *Rhodotorula minuta* IFO 0715, *Trichosporon cataneum* IFO 1198 and the like.

The present invention is more specifically described and explained by means of the following Reference Example and Examples in which all percents are by weight per volume (w/v) unless otherwise noted. It is to be understood that the present invention is not limited to the Examples, and various changes and modifications may be made in the invention without departing from the spirit and scope thereof.

REFERENCE EXAMPLE 1

Synthesis of 5,6-dihydro-4-oxo-(S)-6-methyl-thieno[2,3-b]-thiopyran-7,7-dioxide (S)-3-(2-mercaptothiophene) butyric acid (IV) synthesized according to the process described in U.S. Pat. No. 4,968,814 was converted into 5,6-dihydro-(S)-6-methyl-thieno[2,3-b]thiopyran-4-one(V):

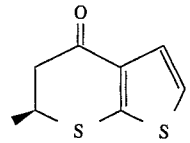

by means of the process described in Japanese Unexamined Patent Publication No. 100174/1989. The synthesized thienothiopyran derivative (V) (274.6 g, 1.49 mol) was dissolved in methanol (3.9 L). An aqueous solution (6.3 L) of Oxone (trade name, commercially available from DuPont CO., LTD.) (1460 g, 2.37 mol) was added dropwise to the reaction mixture over 2 hours with maintaining a temperature at 15° C. After addition, the reaction mixture was stirred for 19 hours at room temperature. To the reaction mixture was then added sodium sulfite (223 g, 1.77 mol) while maintaining the temperature at less than 15° C. The reaction mixture was filtered and the filtrate was extracted three times with ethyl acetate (1.8. L). The cake obtained by filtration was washed with ethyl acetate (3 L). The organic layers were combined and washed with brine. The washed mixture was dried with anhydrous sodium sulfate and decolorized with activated charcoal. The solvent was removed in vacuo to afford 5,6-dihydro-4-oxo-(S)- 6-methyl-thieno[2,3-b]thiopyran-7,7-dioxide (288.3 g).

m.p.: 103.5–104.5° C.

Rf: 0.41 (Ethyl acetate/n-hexane=1/1-$SiO_2$)

IR (KBr, $cm^{-1}$): 1697, 1387, 1313, 1257, 1143, 762, 708, 586, 517

$^1$H-NMR: $CDCl_3$ δ: 7.61(d,J=4.8 Hz, 1H), 7.49(d,J=4.8 Hz, 1H), 3.86(m, 1H), 3.22(m, 2H), 1.57 (d,J=6.8 Hz, 3H)

Example 1

The medium of the following composition was prepared, and 10 ml portions thereof were separately placed in a large-sized test tube and steam-sterilized at 120° C. for 15 minutes.

| Medium composition: | |
|---|---|
| Glucose | 4% |
| Yeast extract | 0.3% |
| $KH_2PO_4$ | 0.1% |
| $(NH_4)_2HPO_4$ | 0.65% |
| NaCl | 0.1% |
| $MgSO_4.7H_2O$ | 0.8% |
| $ZnSO_4.7H_2O$ | 0.06% |
| $FeSO_4.7H_2O$ | 0.09% |
| $CuSO_4.5H_2O$ | 0.005% |
| $MnSO_4.4–6H_2O$ | 0.01% |
| Tap Water | |
| pH 7.0 | |

Each of the microorganisms shown in Table 1 was inoculated in an amount of one loop with a platinum loop into the above medium and cultured with shaking at 30° C. for 24–72 hours. The cells were collected by centrifugation of each culture broth and washed with water. Successively, the cells were suspended in 2 ml of 50 mM phosphate buffer (pH 7.0) and used as the component (1) in the composition of the reaction mixture described below.

| Composition of the reaction mixture: | |
|---|---|
| (1) Cell Suspension | 1 ml |
| (2) 0.1M Phosphate buffer (pH 7.0) | 1 ml |
| (3) 20% Glucose aqueous solution | 0.5 ml |
| (4) 5,6-Dihydro-4-oxo-(S)-6-methyl-thieno[2,3-b]thiopyran-7,7-dioxide | 5 mg |

A test tube was charged with the above-mentioned components (1)–(4) followed by mixing. After mixing, the obtained mixture was subjected to reaction with shaking at 30° C. for 24–72 hours. After completing the reaction, 2.5 ml of acetonitrile was added to each reaction mixture and well-mixed, followed by removal of cells by centrifugation. The supernatant obtained thereby was applied to HPLC (column: Finepak SIL $C_{18-5}$, 4.5×250 mm (commercially available from Nihon Bunko Co. Ltd.), eluent: acetonitrile/$H_2O$=1/1, flow rate: 0.8 ml/min, wave length for detection: 225 nm), and thus the amount of the residual substrate and the amount of the product were determined. Table 1 shows the results. Further, an aliquot of the reaction mixture was subjected to a preparative thin-layer chromatography to isolate the product. The obtained product was analyzed by $^1$H-NMR, to determine a ratio of trans/cis (diastereomer ratio) of 5,6-dihydro-4-hydroxy-(S)-6-methyl-thieno[2,3-b]-thiopyran-7,7-dioxide which was produced. The results are shown in Table 1. The $^1$H-NMR signals of trans-isomer and cis-isomer are as follows:

trans-isomer (4S, 6S); $CDCl_3$, δ: 7.58(d,J=5.2 Hz, 1H), 7.18(d,J=5.2 Hz, 1H), 4.90 (t,J=3.6 Hz, 1H), 3.78(m,1H), 2.70(m,1H), 2.59 (m,1H), 2.36(m,1H), 1.48(d,J=6.8 Hz,$^3$H)

cis-isomer (4R, 6S); $CDCl_3$, δ: 7.58(d,J=4.8 Hz, 1H), 7.16(d,J=4.8 Hz, 1H), 4.87 (q,J=6.0 Hz,10.4 Hz, 1H), 3.44(m,1H), 2.42(m,2H), 2.08–2.20(br, 1H), 1.51(d,J=6.8 Hz,3H)

TABLE 1

| Microorganism | Reaction time (h) | Conversion rate (% by mole) | Ratio of trans/cis |
|---|---|---|---|
| *Ambrosiozyma philentona* IFO 1847 | 48 | 20 | 49/51 |
| *Arthroascus javanesis* | 72 | 33 | 48/52 |

TABLE 1-continued

| Microorganism | Reaction time (h) | Conversion rate (% by mole) | Ratio of trans/cis |
|---|---|---|---|
| IFO 1848 | | | |
| Ashbya gossypii IFO 0560 | 48 | 35 | 53/47 |
| Candida cantarellii IFO 1261 | 24 | 50 | 60/40 |
| Candida guilliermondii IFO 0454 | 48 | 54 | 36/64 |
| Candida intermedia IFO 0761 | 24 | 36 | 40/60 |
| Candida kefyr IFO 0706 | 24 | 49 | 58/42 |
| Candida magnoliae IFO 0705 | 24 | 30 | 53/47 |
| Candida maltosa ATCC 20275 | 24 | 50 | 33/67 |
| Candida maris IFO 10003 | 24 | 18 | 54/46 |
| Candida mogii IFO 0436 | 24 | 28 | 49/51 |
| Candida nusae IFO 1582 | 24 | 31 | 32/68 |
| Candida nodaensis IFO 1942 | 72 | 33 | 43/57 |
| Candida parapsilosis IFO 0585 | 24 | 31 | 50/50 |
| Candida saitoana IFO 0768 | 48 | 20 | 70/30 |
| Candida sorbophila IFO 1583 | 48 | 28 | 47/53 |
| Candida tropicalis IFO 0589 | 24 | 22 | 90/10 |
| Candida tropicalis IFO 1400 | 24 | 25 | 13/87 |
| Candida tropicalis IFO 1404 | 24 | 23 | 57/43 |
| Candida versatilis IFO 1228 | 48 | 31 | 57/43 |
| Cryptococcus albidus IFO 0378 | 48 | 25 | 66/34 |
| Cryptococcus terreus IFO 0727 | 48 | 35 | 72/28 |
| Pichia capsulata IFO 0721 | 48 | 18 | 57/43 |
| Hansenula glucozyma IFO 1472 | 48 | 22 | 58/42 |
| Pichia holstii IFO 0980 | 48 | 33 | 51/49 |
| Pichia minuta IFO 0975 | 48 | 19 | 28/71 |
| Pichia minuta IFO 1473 | 24 | 30 | 70/30 |
| Kluyveromyces marxianus IFO 0288 | 72 | 48 | 60/40 |
| Lipomyces starkeyi IFO 0678 | 24 | 32 | 70/30 |
| Lodderomyces elongisporus IFO 1676 | 48 | 30 | 48/52 |
| Metschnikowia bicuspidata IFO 1408 | 24 | 52 | 70/30 |
| Metschnikowia pulcherrima IFO 0561 | 24 | 50 | 55/45 |
| Metschnikowia reukaufii IFO 0749 | 48 | 33 | 70/30 |
| Pachysolen tannophilus IFO 1007 | 24 | 50 | 48/52 |
| Pichia burtonii IFO 0844 | 48 | 21 | 49/51 |
| Pichia carsonii IFO 0946 | 24 | 22 | 59/41 |
| Pichia toletana IFO 0950 | 48 | 32 | 70/30 |
| Rhodosporidium dacryodium IFO 1930 | 24 | 30 | 52/48 |
| Rhodosporidium sphaerocarpum IFO 1438 | 72 | 20 | 50/50 |
| Rhodosporidium toruloides IFO 0413 | 72 | 18 | 72/28 |
| Rhodotorula glutinis IFO 0395 | 24 | 28 | 37/63 |
| Rhodotorula lactosa IFO 1423 | 24 | 29 | 42/58 |
| Rhodotorula minuta IFO 0928 | 24 | 27 | 50/50 |
| Rhodotorula minuta IFO 0715 | 24 | 53 | 75/25 |
| Saccharomyces cerevisiae IFO 0258 | 72 | 33 | 57/43 |
| Saccharomycopsis crataegensis IFO 1708 | 24 | 49 | 48/52 |
| Saccharomycopsis malanga IFO 1710 | 24 | 49 | 50/50 |
| Schwanniomyces occidentalis IFO 1840 | 24 | 50 | 55/45 |
| Sporidiobolus johnsonii IFO 6903 | 24 | 27 | 26/74 |
| Sporobolomyces pararoseus IFO 0471 | 48 | 30 | 23/77 |
| Stephanoascus ciferrii IFO 1854 | 48 | 17 | 75/25 |
| Trigonopsis variabilis IFO 0671 | 24 | 51 | 69/31 |
| Trichosporon cataneum IFO 1198 | 24 | 53 | 80/20 |
| Wingea robertsii IFO 1277 | 24 | 20 | 37/63 |

Example 2

The medium of the composition shown in Example 1 was prepared and divided into 50 ml portions. Ten portions were charged into a 2 liter Sakaguchi flask and steam-sterilized at 120° C. for 20 minutes. An amount of one loop of *Candida tropicalis* IFO 0589 was inoculated with a platinum loop into 10 ml of the culture medium of the composition shown in Example 1 in a large-sized test tube, and precultured with shaking at 30° C. for 24 hours. One ml of thus obtained culture broth of *Candida tropicalis* IFO 0589 was inoculated into the culture medium and cultured with shaking at 30° C. for 24 hours. The cells were collected by centrifugation of the culture broth and washed with water. The cells were then suspended into a saline to make a final volume 200 ml. A three neck flask having a content volume of 1 L was charged with 200 ml of thus obtained cell suspension, 50 ml of a 40% glucose aqueous solution and 250 ml of water, and then pH of the mixture was adjusted to pH 6.5 with sodium hydroxide. Thereto was added 2.5 g of 5,6-dihydro-4-oxo-(S)-6-methyl-thieno[2,3-b]-thiopyran-7,7-dioxide, and then the reaction was carried out at 30° C. for 24 hours with aerobically stirring. After completion of the reaction, 15 g of Hyflo Super-Cel (trade name, commercially available from John-Manville Sales Corporation) and 200 ml of ethyl acetate were added to the reaction mixture. After stirring, the cells were removed by filtration. The filtrate was then separated to an aqueous layer and an organic layer, and then the aqueous layer was extracted twice with 100 ml of ethyl acetate. The organic layers were combined and dried with anhydrous sodium sulfate, followed by decolorization with 2.5 g of activated charcoal. The solvent was distilled away under a reduced pressure to give a total volume of 100 ml of condensation product. To the condensate was added 100 ml of toluene, further the mixture was concentrated to give a total volume of 80 ml. The deposited crystal was filtrated and dried to give 1.22 g of (4S, 6S)-5,6-dihydro- 4-hydroxy-6-methyl-thieno-[2,3-b]thiopyran-7,7-dioxide.

m.p.: 118–120.5° C.

Rf: 0.42 (Ethyl acetate-$SiO_2$)

IR (KBr, $cm^{-1}$): 3503, 1:414, 1306, 1142, 1130, 1051, 668, 603, 547, 528

$^1$H-NMR: $CDCl_3$ δ: 7.58(d,J=5.2 Hz, 1H), 7.18(d,J=5.2 Hz, 1H), 4.90 (t,J=3.6 Hz, 1H), 3.78(m,1H), 2.70(m,1H), 2.59 (m,1H), 2.36 (m,1H), 1.48(d,J=6.8 Hz,3H)

$[α]^{20}_D$=−81.1(c=1.0,$CH_3OH$)

In addition to the ingredients used in the Examples, other ingredients can be used in the Examples as set forth in the specification to obtain substantially the same results.

What we claim is:

1. A process for preparing trans-(4S, 6S)-5,6-dihydro-4-hydroxy-6-methyl-thieno[2,3-b]thiopyran-7,7-dioxide having the formula (IIb):

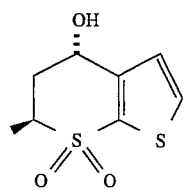

(IIb)

in a trans/cis ratio of at least 50/50, which comprises subjecting 5,6-dihydro-4-oxo-(S)-6-methyl-thieno[2,3-b]thiopyran-7,7-dioxide having the formula (I):

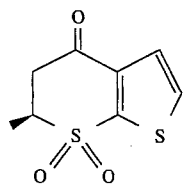

(I)

to the action of a microorganism to reduce the thienothiopyran derivative having the formula (I), to obtain the trans-(4S, 6S)-isomer of 5,6-dihydro-4-hydroxy-(S)-6-methyl-thieno-[2,3-b]thiopyran-7,7-dioxide having the formula (II):

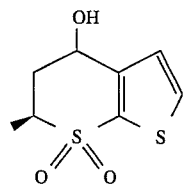

(II)

in a trans-(4S, 6S)/cis-(4R, 6S) ratio of at least 50/50, wherein said microorganism is a member selected from the group consisting of *Ashbya gossypii* IFO 0560, *Candida cantarellii* IFO 1261, *Candida kefyr* IFO 0706, *Candida magnoliae* IFO 0705, *Candida maris* IFO 10003, *Candida parapsilosis* IFO 0585, *Candida saitoana* IFO 0768, *Candida tropicalis* IFO 0589, *Candida tropicalis* IFO 1404, *Candida versatilis* IFO 1228, *Cryptococcus albidus* IFO 0378, *Cryptococcus terreus* IFO 0727, *Pichia capsulata* IFO 0721, *Hansenula glucozyma* IFO 1472, *Pichia holstii* IFO 0980, *Pichia minuta* IFO 1473, *Kluyveromyces marxianus* IFO 0288, *Metschnikowia bicuspidata* IFO 1408, *Metschnikowia pulcherrima* IFO 0561, *Metschnikowia reukaufii* IFO 0749, *Pichia carsonii* IFO 0946, *Pichia toletana* IFO 0950, *Rhodosporidium dacryodium* IFO 1930, *Rhodosporidium sphaerocarpum* IFO 1438, *Rhodosporidium toruloides* IFO 0413, *Rhodotorula minuta* IFO 0928, *Rhodotorula minuta* IFO 0715, *Saccharomyces cerevisiae* IFO 0258, *Saccharomycopsis malanga* IFO 1710, *Schwanniomyces occidentalis* IFO 1840, *Stephanoascus ciferrii* IFO 1854, *Trigonopsis variabilis* IFO 0671 and *Trichosporon cataneum* IFO 1198.

* * * * *